United States Patent [19]

Macri

[11] Patent Number: 4,734,438

[45] Date of Patent: Mar. 29, 1988

[54] NOREPINEPHRINE POTENTIATED COMPOSITIONS AND METHOD OF USE

[76] Inventor: Frank J. Macri, 3602 Janet Rd., Silver Spring, Md. 20906

[21] Appl. No.: 844,596

[22] Filed: Mar. 27, 1986

Related U.S. Application Data

[60] Division of Ser. No. 722,177, Apr. 10, 1985, Pat. No. 4,581,376, which is a continuation of Ser. No. 488,690, Apr. 26, 1983, abandoned.

[51] Int. Cl.$^4$ ............................................. A61K 31/135
[52] U.S. Cl. .................................... 514/653; 514/913
[58] Field of Search ................... 424/45; 514/653, 913

[56] References Cited

U.S. PATENT DOCUMENTS

| | | | |
|---|---|---|---|
| 3,679,804 | 7/1972 | Grunwaldt | 424/308 |
| 3,808,317 | 4/1974 | Hecht et al. | 514/913 |
| 4,275,074 | 6/1981 | Langham | 424/280 |
| 4,469,706 | 9/1984 | Nathanson | 514/913 |
| 4,581,376 | 4/1986 | Macri | 514/913 |
| 4,652,586 | 3/1987 | Nathanson | 514/913 |

FOREIGN PATENT DOCUMENTS 2052991  3/1971  Fed. Rep. of Germany .

OTHER PUBLICATIONS

Chem. Abst. 90:115264q (1979)–Patter et al.
Chem. Abst. 78 52709(t)(1973)–Neufeld et al.
Glaucoma Update: Krieglstein et al., pp. 19–26 (1979).
Chem. Abst. 88 99553(j)(1978)–Neeters.
Chem. Abst. 95 126085(m)(1981)–Innemee et al.
Chem. Abst. 98 191598(g)(1983)–Miichi et al.
Gaasterland et al, "Studies of Aqueous Humor Dynamics in Man", *Investigative Ophthalmology*, vol. 12, No. 4, Apr. 1983, pp. 267–279.
Rote Liste, 1965, pp. 126, 127, 92, 93, 46, 47, Editio Cantor, Aulendorf/Wortt., DE.
Merck Index (1960) pp. 57, 58, 395 § 608.
Douglas Gaasterland, et al., "Studies of Aqueous Humor Dynamics in Man III. Measurements in Young Normal Subjects Using Norepinephrine and Isoproterenol".
Duke-Elder, "Glaucoma in System of Ophtholomogy", vol. XI, Henry Kimpton, Lond., 1969.
Frank J. Macri, et al., "The Formation and Inhibition of Aqueous Humor Production", Arch Opthalmol, vol. 96, Sep. 1978.

*Primary Examiner*—Douglas W. Robinson
*Attorney, Agent, or Firm*—Lorusso & Loud

[57] ABSTRACT

Novel pharmaceutical compositions containing norepinephrine releasers such as alpha-adrenergic agonists, para-sympathomimetic agonists and carbonic anhydrase inhibitors in combination with a potentiating amount of norepinephrine are disclosed. Use of such compositions, exemplified by the combination of norepinephrine and epinephrine, in an ophthalmic solution for the treatment of glaucoma is also disclosed, as well as the use of the combination of norepinephrine and a norepinephrine releaser in the treatment of congestion in the upper respiratory tract.

8 Claims, No Drawings

NOREPINEPHRINE POTENTIATED COMPOSITIONS AND METHOD OF USE

This is a division of application Ser. No. 722,177 filed Apr. 10, 1984, now U.S. Pat. No. 4,581,376 which, in turn, is a continuation of application Ser. No. 488,690 filed Apr. 26, 1983 and now abandoned.

BACKGROUND OF THE INVENTION

1. Field of the Invention

The present invention relates to pharmaceutical compositions containing an active agent having a modality of action whereby sympathetic neuron terminals are stimulated and l-norepinephrine is released and to methods for treating glaucoma, nasal congestion, chest congestion, etc. using such compositions.

2. The Prior Art

Glaucoma is a term used to describe various eye disorders resulting from excessive intraocular pressure. Intraocular pressure is maintained at specific levels by a combination of two factors: (1) the rate at which aqueous humor is formed and (2) the rate at which aqueous humor leaves the eye. If the rate at which aqueous humor is formed can be reduced, then a decrease in eye pressure should be anticipated. Likewise, if the rate of aqueous humor outflow can be increased, the eye pressure should again decline.

Earlier reports have indicated that drugs of many modalities of action were able to lower eye pressure of glaucomatous patients Such drugs include α-adrenergic agonists, β-adrenergic agonists, β-adrenergic blockers, p-sympathomimetic agonists and carbonic anhydrase inhibitors. Agents included in all of these groups have been reported to decrease the rate of aqueous humor formation in the eye.

In a previously published article "The Formation and Inhibition of Aqueous Humor Production", *Archives of Ophthalmology*, Vol. 96, September 1978, pp. 1664-1667, the present applicant and S. J. Cevario disclosed data indicating that certain sympathomimetic agents, acetazolamide (a carbonic anhydrase inhibitor) and ouabain (a cardiac glycoside) operate a vasoconstrictors to inhibit aqueous humor production through a mechanism by which the drugs stimulate intraocular receptors "E-1" which, in turn, communicate with neuronal terminals where norepinephrine is released for the stimulation of adjoining α-adrenergic receptor sites. All drugs operating by such a mechanism may be considered "norepinephrine releasers". Among the sympathomimetic agents, epinephrine is perhaps most widely used in the treatment of chronic simple (wide-angle) glaucoma. However, several problems are commonly encountered in the treatment of glaucoma with epinephrine compositions. The drug is not always continuously effective. Prolonged use of epinephrine in the 1-4% concentrations of commercial ophthalmic solutions leads to pigmentation (sedimentation of the oxidized drug) and maculopathy. Moreover, narrow-angle glaucoma is a contraindication for epinephrine because, in commercial concentrations, epinephrine produces dilation of the pupil which further narrows the angle thereby exacerbating the condition.

Various sympathomimetic drugs, have also been used in commercially available preparations for the relief of nasal and chest congestion. In addition to finding utility in ophthalmic solutions for the treatment of simple ("open-angle" or "wide-angle") glaucoma, epinephrine has been used as the active agent (bronchodilator) in sprays for the temporary relief of the paroxysms of bronchial asthma. Phenylephrine has also been used in tablets and syrups and topical sprays for the relief of nasal and chest congestion, as well as in the treatment of glaucoma. Ephedrine finds extensive use as a bronchodilator in tablets, syrups and topical mists. In conventional pharmaceutical preparations these compounds are most commonly used in salt form, e.g., hydrochloride, hydrobromide, bitartrate or tannate.

One of the problems with the clinical use of the above mentioned drugs is that, within time, tachyphylaxis develops, i e., the drugs become ineffective or remain only moderately effective. For example with regard to epinephrine, *Remington's Pharmaceutical Sciences* (16th Ed. 1980), p. 824 states "As a topical decongestant it causes too much aftercongestion to be a first-line drug."

l-norepinephrine is a hormone which naturally occurs in the human body and is the essential neuro transmitter of sympathetic activity in the peripheral nervous system. l-norepinephrine, also known as levarterenol, l-noradrenaline and l-arternal, is classified as an α-adrenergic agonist and its chief physiological function is that of vasoconstriction. The chief medical uses of l-norepinephrine are in the treatment of hypotension and shock due to impaired vasomotor activity.

Norepinephrine has been considered to have no clinical value in the treatment of glaucoma on the basis of findings that it has negligible effect in reducing ocular tension. Duke-Elder, *System of Ophthalmology*, Vol. XI, p. 518. Gaasterland et al in "Studies of Aqueous Humor Dynamics in Man", *Investigative Ophthalmology*, Vol. 12, No. 4, April 1973, pp 267-279, disclose the results of studies of the effects on aqueous humor dynamics in humans using a 2% sterile solution of norepinephrine as an alpha-adrenergic stimulator, a 1% sterile solution isoproterenol hydrochloride as a beta-adrenergic stimulator, a 2% sterile solution of l-epinephrine bitartrate (an alpha and beta stimulator) and a combination of the norepinephrine and isoproterenol solutions. The combination provided an effect described as similar to that achieved with epinephrine which is both an alpha and beta agonist. The study concluded that "the acute effect of epinephrine in young normal stubjects is comprised of two parts—reduction of aqueous flow due to beta-adrenergic receptor stimulation and reduction of pseudofacility due to alpha-adrenergic receptor stimulation, and that the reduction of intraocular pressure is secondary to the addition of these two effects. " A comparison of the data of Gaasterland et al for the combined use of isoproterenol and norepinephrine with that for isoproterenol alone indicates that the use of norepinephrine inhibited the effectiveness of isoproterenol in lowering aqueous humor production and intraocular pressure. Administration of norepinephrine alone produced "no significant change" in intraocular pressure and produced an increase in aqueous flow.

SUMMARY OF THE INVENTION

It has now been discovered that a relatively small amount of locally applied norepinephrine serves to potentiate the pharmacologic activity of a wide range of norepinephrine releasers. This potentiating effect is particularly evident for compositions containing low levels of the norepinephrine releaser, e.g., 0.5 wt. % or less. The term "norepinephrine releaser", as used herein to describe the pharmacologic activity of various active ingredients used in the compositions and methods of the present invention, is unique and is defined by the individual ability of hexamethonium and tolazoline to block the pharmacologic activity of that agent. See Frank J. Macri, "Local Ganglion-like Stimulating Properties of Some Adrenergic Amines which Affect Blood Vessels of the Anterior Segment of the Eye", Investigative Ophthalmology, Vol. 11, No. 10, pp. 838-844, Oct. 1972, the teachings of which are incorporated herein by reference.

It is to be anticipated that systemic or oral administration of the combined drugs would not be potentiative since norepinephrine is rapidly destroyed by blood enzymes. Accordingly, the present invention contemplates local or topical administration only. In contrast, with local administration, the drugs are able to reach the α-adrenergic receptors, which when stimulated produce a lowering of aqueous humor production, broncho-dilation and nasal vasoconstriction. The present inventor has discovered that the aqueous humor action of epinephrine when administered to the eye is blocked by hexamethonium whereas hexamethonium potentiates the blood pressure elevating action of epinephrine administered intravenously. Accordingly, the mode of action of the norepinephrine releaser in the eye differs from the traditionally accepted mode of action, i.e., its mode of action on the circulatory system. Further it is now believed that a norepinephrine releaser, as described herein, administered topically (directly) to the nasal or lung tissue behaves pharmacologically in the same manner as when applied to the cornea.

Studies conducted by the applicant indicate that the loss of activity commonly seen in the administration of conventional drugs which may be characterized as norepinephrine releasers is due to the complete or partial loss of endogenous neuronal stores of norepinephrine. Elementary logic dictates that if the stores of releasable norepinephrine at the nerve terminals is diminished or depleted, then the agents wich act by releasing norepinephrine become proportionately less effective. The present invention provides repletion of the norepinephrine stores in the nerve terminals and thereby (1) prevents the loss of pharmacologic activity of the norepinephrine releaser (tachyphylaxis) and (2) potentiates the response to the norepinephrine releaser by providing a higher concentration of localized norepinephrine released during a fixed stimulus.

Accordingly, the present invention provides a variety of pharmaceutical compositions containing norepinephrine and an alpha-adrenergic agonist, a para-sympathomimetic agonist, or a carbonic anhydrase inhibitor. The pharmacologic activity of such norephinephrine releasers is significantly potentiated simply by adding a relatively small amount of norepinephrine to a conventional pharmaceutical preparation containing the norepinephrine releaser.

Various compositions of the present invention, for example, those containing ephedrine and/or epinephrine in combination with norepinephrine, also find utility as bronchodilators in the treatment of bronchospasms associated with acute and chronic bronchial asthma, pulmonary emphysema, bronchitis and bronchiectasis. Accordingly, the present invention contemplates use of the combination of norepinephrine and a norepinephine releaser in a wide variety of types of medications including mists designed for topical application in the relief of nasal and bronchial congestion; nose drops; and as ophthalmic solutions for the treatment of the symptoms of glaucoma, red eye, etc.

One particular advantage of the present invention is that it allows a norepinephrine releaser to be used in ophthalmic solutions at low concentrations whereby the aforementioned problems of pigmentation and maculopathy are avoided while the potency in the relief of the symptoms of simple (open angle) glaucoma are retained at a level formerly seen only in application of solutions containing on the order of 2 percent by weight of the drug. More importantly, the ophthalmic solutions of the present invention, containing relatively low concentrations of epinephrine may also be used in the treatment of narrow angle glaucoma because at such low concentrations, i.e., about 0.1% or lower, the pupil is not significantly dilated and the symptom is not thereby exacerbated, yet the underlying condition (excessive pressure) is effectively treated.

The amount of norepinephrine releaser in the compositions of the present invention is preferably 0.5 wt. % or less. Typically, the compositions will contain 0.001-0.5 wt. % of the norepinephrine releaser and 0.0001-0.05 wt. % norepinephrine. Typically, the ratio of the norepinephrine to the norepinephrine releaser is about 1:10 or less.

The methods of the present invention involve the simultaneous application of both the norepinephrine and the norepinephrine releaser. The methods of the present invention involve the use of pharmaceutical compositions containing a combination of those two active agents in the relief of nasal and chest congestion, i.e., congestion in the upper respiratory tract, and in the treatment of both wide angle and narrow angle glaucoma. Ophthalmic solutions containing the norepinephrine releaser at a concentration of about 0.1% or less and a potentiating amount of norepinephrine may be used for the treatment of both wide and narrow angle glaucoma. The term "simultaneous" as used herein, has reference to the application of norepinephrine and the norepinephrine releaser together in a concomitant administration as well as separate administrations of the norepinephrine and the norepinephrine releaser, e.g., within about one-hour, preferably within 5-10 minutes or less.

In another of its aspects, the present invention provides separate compositions containing norepinephrine and a norepinephrine releaser, respectively, together in kit form.

Accordingly, it is an object of the present invention to provide compositions in which the pharmacological activity of a norepinephrine releaser is potentiated by the inclusion of norepinephrine and methods of utilizing such compositions.

It is a further object of the present invention to allow the use of norepinephrine releasers in lower concentrations while retaining the level of pharmacologic activity commonly provided by conventional preparations containing such agents, thereby minimizing undesirable side effects.

These and other objects and features of the present invention will become apparent from the detailed description of the invention to follow.

DESCRIPTION OF THE PREFERRED EMBODIMENTS

Norepinephrine releasers having pharmacological activity which is enhanced by co-administration with norepinephrine in accordance with the present invention include, for example:

α-adrenergic agonists:

epinephrine
mephentermine
methoxamine
ephedrine
hydroxyamphetamine
β-adrenergic agonists:
 isoproterenol
p-sympathomimetic agonists:
 pilocarpine
carbonic anhydrase inhibitors:
 acetazolamide Of the above, those groups exclusive of the β-adrenergic agonists are preferred because of adverse side-effects on the heart produced by the β-adrenergic agonists. Also, as previously noted, Gaasterland et al reported that the effects of isoproterenol in reducing aqueous humor flow and eye pressure, in a 1 wt. % ophthalmic solution are not potentiated by norepinephrine and, on contrary, are reduced somewhat. However, it has now been discovered that at lower concentrations on the order of 0.01 wt. %, the effects of isoproterenol are potentiate by norepinephrine. Also, it is believed that at isoproterenol concentrations of 0.1–0.01 wt. % or less the potential for adverse side-effects on the heart from use of the β-adrenergic agonist in an ophthalmic solution is reduced to insignificance.

As previously noted, the compositions of the present invention include ophthalmic solutions for treament of glaucoma, red eye, etc. The ophthalmic solutions of the present invention contain norepinephrine and a nonepinephrine releaser in a sterile liquid carrier. As is conventional in pharmaceutical practice, the sterile liquid carrier will typically be a buffered isotonic solution in either an aqueous or a viscous, e.g., methylcellulose, vehicle. Also in accordance with conventional practice, such ophthalmic solutions may contain an antiseptic preservative such as benzalkonium chloride and an antioxidant such as sodium bisulfite or ascorbic acid. A typical formulation for such an isotanic ophthalmic aqueous solution, buffered to a pH of 4.4 with a sodium citrate-citric acid buffer solution and containing:

0.1 weight % epinephrine bitartrate
0.01 weight % norepinephrine
0.15 weight % sodium bisulfite
1:7500 benzalkonium chloride Sodium chloride is typically added to adjust the osmolality, e.g., to 288 mosm. (Gaasterland et al).

The combination of norepinephrine with epinephrine is considered particularly useful because of the body's high level of tolerance for these substances, both of which are hormones produced naturally within the body. Accordingly, it is believed that side effects from use of such a composition are negligible.

The compositions intended for use in the relief of nasal and/or chest congestion likewise contain the norepinephrine releaser and norepinephrine in combination with a conventional pharmaceutical carrier, e.g., aqueous solutions and inert propellants such as halogenated hydrocarbons for bronchial sprays.

The examples which follow serve to illustrate the potentiating effect of norepinephrine on the pharmacologic activity of epinephrine in ophthalmic solutions.

EXAMPLES

The following test results demonstrate the effectiveness of the compositions of the present invention in decreasing the rate of aqueous humor formation in the eye and indicate effectiveness in the treatment of glaucoma. Rabbit eyes, freshly removed from their hosts, were arterially perfused and placed in individual holders. The rate of spontaneous formation of aqueous humor was measured over a period of 0.5 hour to determine the control response values reported in column (3) of the table below. Measurement for the controls and the drug tests employed the procedure and apparatus described in an article co-authored by the present applicant and J. O'Rouke entitled "Measurements of Aqueous Humor Tunover Rates Using a Gamma Probe" published in

*Archives of Ophthalmology*, Vol. 83 (1970), pp 741–746, the teachings of which are incorporated herein by reference. In testing norepinephrine alone (Cols. 8 and 9), l-epinephrine alone (cols. 4 and 5) and the combination thereof (Cols. 6 and 7), 50 microliters (50 μl) of each drug or drug combination was placed on the cornea, i.e., topically applied, at the end of the control period and the monitoring of the rate of aqueous humor formation with the gamma probe was continued for an additional 30 minutes. The values for "Response" reported under column headings 5, 7 and 9 are for the rate of aqueous humor formation as measured 30 minutes after drug administration. The results clearly show that relatively small amounts of norepinephrine greatly enhance the effectiveness of the epinephrine in decreasing the rate of aqueous humor formation.

The various administrations in each experiment were consecutive. Thus for Exp. 210 the response 2.6(5) was obtained 30 minutes after the first administration of l-epinephrine and the response 2.7(5) was obtained after a second application of epinephrine. In each case where a second application is shown, the second application followed the first by 30 minutes. Further the application of l-epinephrine and norepinephrine in combination (6) followed the administration of epinephrine by 30 minutes. Thus, the results for experiments employing dual applications of epinephrine alone show that the potentiated composition of the present invention was effective to further lower aqueous humor production even after the maximum effect of epinephrine alone had been realized. The ineffectiveness of norepinephrine alone, in the concentration used, is shown in Exp. Nos. 170–227.

| | | | Aqueous Humor Formation Rates Microliters per Minute | | | | | | |
|---|---|---|---|---|---|---|---|---|---|
| | Pre- | | | | | | | l-Norepinephrine | |
| Exp. No. (1) | Treatment (1) | Conc. (%) (2) | Control Response (3) | Conc. (%) (4) | Response (5) | Conc. (%) (6) | Response (7) | Conc. (%) (8) | Response (9) | % of Control (10) |
| | | | | l-epinephrine | | l-epinephrine/ l-norepinephrine | | | | |
| 210 | | | 6.0 | .01 | 2.6 | 0.01/ .001 | 2.0 | | | |
| | | | | .01 | 2.7 | | | | | |
| 168 | | | 5.3 | 0.1 | 4.5 | 0.01/ 0.001 | 3.1 | | | |

-continued

| Exp. No. | Pre-Treatment (1) | Conc. (%) (2) | Control Response (3) | Conc. (%) (4) | Response (5) | Conc. (%) (6) | Response (7) | l-Norepinephrine Conc. (%) (8) | Response (9) | % of Control (10) |
|---|---|---|---|---|---|---|---|---|---|---|
| 215 | | | 5.9 | .001 | 5.2 | 0.001/0.0001 | 2.9 | | | |
| 216 | | | 3.3 | .001 | 2.5 | 0.001/0.0001 | 1.4 | | | |
| 218 | | | 7.4 | .001 | 2.6 | 0.001/0.0001 | 1.5 | | | |
|  |  |  |  | .001 | 3.1 |  |  |  |  |  |
| 217 | l-epi | .001 | 3.6 | .001 | 3.7 | 0.001/0.0001 | 2.4 | | | |
| 219 | l-epi | .001 | 4.3 | .001 | 5.8 | 0.001/0.0001 | 3.0 | | | |
|  |  |  |  | .001 | 5.4 |  |  |  |  |  |
| 129 | l-NE | .001 | 4.2 | | | 0.01/0.001 | 1.4 | | | |
| 131 | l-NE | .001 | 2.3 | | | | | .001 | 2.5 | 108 |
| 170 | | | 8.3 | | | | | .001 | 7.9 | 95 |
| 171 | | | 4.5 | | | | | .001 | 3.0 | 67 |
| 147 | | | 1.9 | | | | | .001 | 1.6 | 84 |
|  |  |  |  |  |  |  |  |  | mean | 88.5 |
| 223 | | | 2.2 | | | | | .0001 | 2.2 | 100 |
| 224 | | | 4.8 | | | | | .0001 | 4.3 | 90 |
| 226 | | | 5.8 | | | | | .0001 | 6.0 | 103 |
| 227 | | | 2.5 | | | | | .0001 | 2.4 | 96 |
|  |  |  |  |  |  |  |  |  | mean | 97.2 |
|  |  |  |  | l-Isoproterenol |  | l-Isoproterenol + l-Norepinephrine |  |  |  |  |
| 166 | | | 7.3 | .01 | 7.2 | .01/.001 | | | 3.2 | | l-epi = l-epinephrine
l-NE = l-norepinephrine

Although, only l-isomers have been utilized in experimentation to date, it is anticipated that the d,l-isomeric forms would be also active due to their content of the l-isomers.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A pharmaceutical composition comprising: (1) 0.1–0.01 wt % isoproterenol or a pharmaceutically aceptable salt thereof; and (2) 0.0001–0.05 wt % l-norepinephrine or a pharmaceutially acceptable salt thereof.

2. The composition of claim 1 wherein the ratio of isoproterenol or pharmaceutically aceptable salt thereof to norepinephrine or pharmaceutically acceptable salt thereof is about 10:1.

3. An opthalmic solution comprising: (1) 0.1–0.01 wt % isoproterenol or a pharmaceutically acceptable salt thereof; (2) 0.0001–0.05 wt % norepinephrine or a pharmaceutically acceptable salt thereof; and (3) a sterile, pharmaceutically acceptable liquid carrier.

4. The composition of claim 3 wherein the ratio of isoproterenol or pharmaceutically acceptable salt thereof to norepinephrine or pharmaceutically aceptable salt thereof is about 10:1

5. A method for the treatment of glaucoma by simultaneously, topically administering to the eye a solution of 0.1–0.01 wt % isoproterenol or a pharmaeutically acceptable salt thereof and a solution of 0.0001–0.05 wt % norepinephrine or a pharmaceutically acceptable salt thereof.

6. The method of claim 5 wherein said norepinephirne or a pharmaceutically aceptable salt thereof and isoproterenol or a pharmaceutically acceptable salt thereof are co-administered in the same sterile, pharmaceutical liquid carrier.

7. The method of claim 5 wherein said norepinephrine or a pharmaceutically acceptable salt thereof and isoproterenol or a pharmaceutically acceptable salt thereof are administered in separate sterile, pharmaceutical liquid carriers.

8. The method of claim 5 wherein the ratio of isoproterenol or pharmaceutically acceptable salt thereof to norepinephrine or pharmaceutically acceptable salt thereof is about 10:1.1

* * * * *

UNITED STATES PATENT AND TRADEMARK OFFICE
CERTIFICATE OF CORRECTION

PATENT NO. : 4,734,438
DATED : March 29, 1988
INVENTOR(S) : Frank J. MACRI

It is certified that error appears in the above—identified patent and that said Letters Patent is hereby corrected as shown below:

Col. 1, line 31, after "patients" insert --.--;

line 43, "a", second occurrence" should read --as--;

line 50, after "Norepinephrine releasers." begin new paragraph.

Col. 3, lines 6 and 7 "Investigative Ophthalmology," should read "Investigative Ophthalmology";

line 38, "wich" should read --which--.

Col. 5, line 22, "potentiate" should read --potentiated--.

Col. 6, line 23, after "in" continue with paragraph.

Claim 1, line 3, "aceptable" should read --acceptable--.

Claim 2, line 2, "aceptable" should read --acceptable--.

Claim 5, line 3, "pharmaeutically" should read --pharmaceutically--.

UNITED STATES PATENT AND TRADEMARK OFFICE
CERTIFICATE OF CORRECTION

PATENT NO. : 4,734,438

DATED : March 29, 1988

INVENTOR(S) : Frank J. Macri

It is certified that error appears in the above-identified patent and that said Letters Patent is hereby corrected as shown below:

Claim 6, line 2, "aceptable" should read -- acceptable --.

Signed and Sealed this

Nineteenth Day of July, 1988

*Attest:*

DONALD J. QUIGG

*Attesting Officer*    *Commissioner of Patents and Trademarks*